United States Patent [19]

Morita

[11] Patent Number: 5,110,594

[45] Date of Patent: May 5, 1992

[54] INSECTICIDES AND BACTERICIDE MADE OF SELL FLOWER ESSENTIAL OIL

[76] Inventor: Dai Morita, 96-1,2-chome, Ishimine-cho, Shuri, Naha-shi, Okinawa-ken, Japan

[21] Appl. No.: 622,050

[22] Filed: Dec. 4, 1990

[51] Int. Cl.$^5$ ............................................. A01N 25/00
[52] U.S. Cl. .................................... 424/405; 424/405; 424/406; 424/408; 424/195.1
[58] Field of Search ............. 424/405, 406, 408, 195.1

[56] References Cited

U.S. PATENT DOCUMENTS 4,170,631 10/1979 Young et al. .................. 424/19

Primary Examiner—Thurman K. Page
Assistant Examiner—Louis A. Piccone
Attorney, Agent, or Firm—Armstrong, Nikaido, Marmelstein, Kubovcik & Murray

[57] ABSTRACT

Volatile oil extracted from sell flower growing in the wild is diluted with a solvent to about 2% and directly immersed into a sheet material such as paper, cloth or the like or adsorbed into adsorption particles and mixed into paper, for example, whereby sheet-like insecticides and bactericides made of sell flower essential oil are obtained. The insecticides and bactericides made of the sell flower essential oil have insecticide, fungicide, antimold and antibacterial effects and are effective as antivermin and antibacterial agents and harmful living-thing impeding agents. As a carrier, a mixture of one or two kinds or more of diatomaceous earth, alumina or the like, or various kinds of synthetic resins are used, and sell flower essential oil is immersed or blended therein whereby granular insecticides and bactericides are obtained. An emulsifier, a dispersion agent, a suspension agent, a wetting agent, a stabilizer or the like is added according to the intended use to be in the form of an oil agent, an emulsion, a hydrate, a powdery agent, a tablet, a gelling agent, a jetting agent or the like.

9 Claims, 1 Drawing Sheet

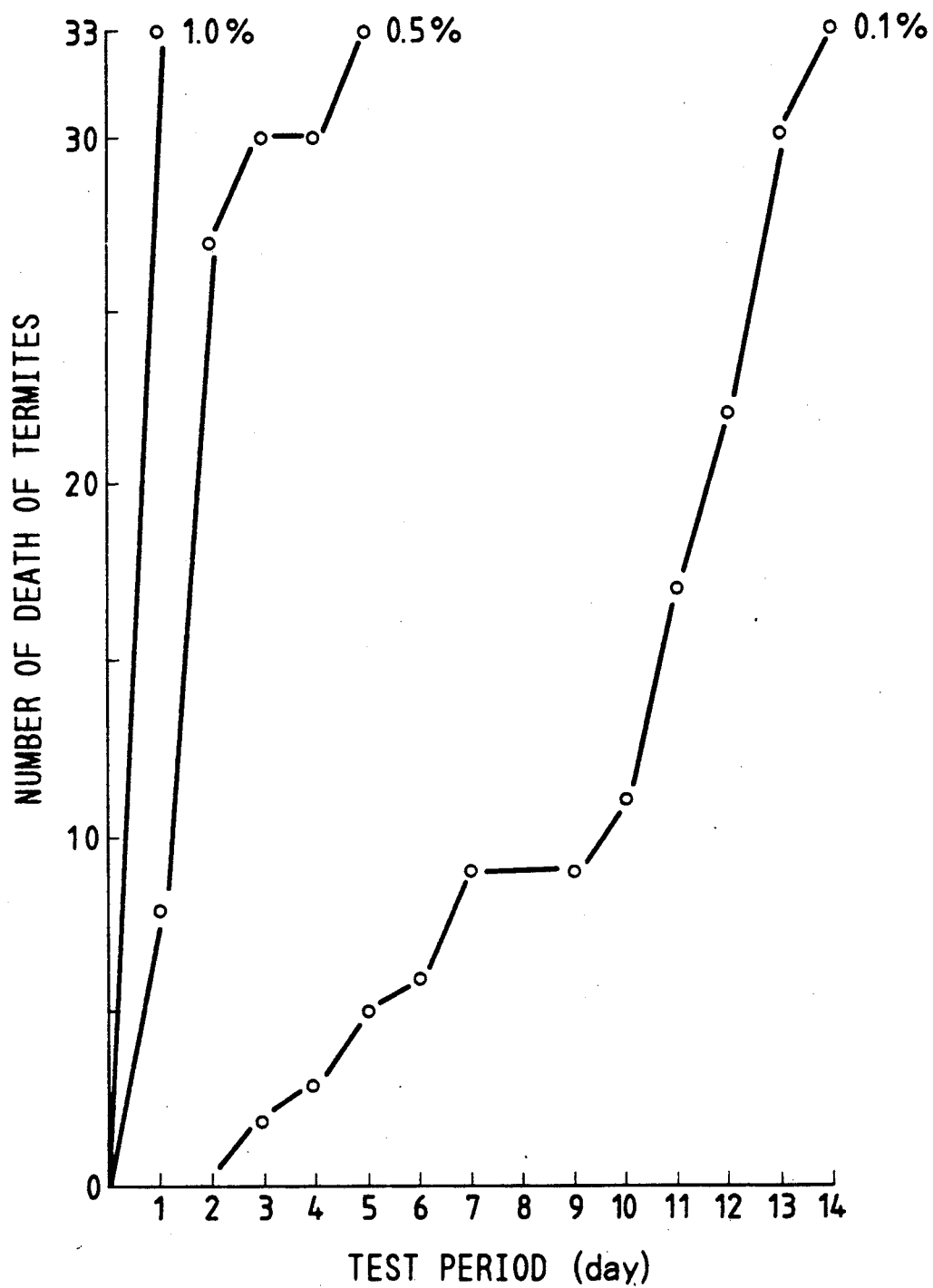

INSECTICIDES AND BACTERICIDE MADE OF SELL FLOWER ESSENTIAL OIL

BACKGROUND OF THE INVENTION (1) Field of the Invention

The present invention relates to insecticides and bactericide, which have insecticide, fungicide, antimold and antibacterial effects, made of essential oil extracted from sell flower.

(2) Description of the Prior Art

Sell flower, which belongs to a giner family alpinia genus and has a botanical name of Alpinia Speciosa K. schum, grows in subtropical zones, for example, south west islands such as Amami Ohshima, Okinawa, etc. in Japan. Its leaves have a unique aroma, and are therefore used to wrap rice cakes. Also, it has been found that Japanese paper having a unique hand and feel is obtained from fibers of sell flower which are used as a raw material in Japanese paper.

However, it has not been known that the sell flower had antivermin, insecticide and antibacterial properties. Sell flower has not been used for uses other than those as mentioned above. The present inventors have found during their study of sell flower that sell flower has excellent antivermin, insecticide and bacterial effects and have made further studies. As a result, the inventors have succeeded in extracting sell flower essential oil which is material to the insecticide, bactericide, antivermin and bacterial effects and have used it for the purpose of an insecticide, bactericide, antivermin and antibacteria composition.

SUMMARY OF THE INVENTION

An object of the present invention is to provide insecticides and bactericides, which have high insecticide, bactericide, antivermin and antibacterial effects, are inexpensive and can be applied in various forms, using essential oil obtained from sell flower.

Another object of the present invention is to provide insecticides and bactericides obtained by forming sell flower essential oil into pellets.

A further object of the present invention is to provide sheet-like insecticides and bactericides in which sell flower essential oil is immersed into or dispersed in a sheet material.

The insecticides and bactericides made of sell flower oil according to the present invention for achieving the aforementioned objects make use of sell flower essential oil which can be extracted from sell flower which grows in the wild. The aforesaid sell flower essential oil has been analyzed and as a result it has been found to contain therein components as follows:

| Component | Weight % |
| --- | --- |
| Ethyl alcohol | 0.04 |
| Alpha-pinene | 7.00 |
| Camphene | 3.39 |
| Beta-pinene | 2.41 |
| (+)-3-carene | 0.25 |
| 1-penten-3-OL | 0.01 |
| Myrcene | 1.76 |
| Alpha-phellandrene | 0.12 |
| Alpha-terpinene | 0.04 |
| Limonene | 5.75 |
| Beta-phellandrene | 7.00 |
| 1,8-cineol | 16.12 |
| Gamma-terpinene | 0.15 |
| P-cymene | 17.69 |

-continued

| Component | Weight % |
| --- | --- |
| Terpinolene | 0.05 |
| CIS-3-hexenol | 0.10 |
| Alpha-P-dimethylstylene | 0.02 |
| Linalool oxide-1 | 0.04 |
| Linalool oxide-2 | 0.04 |
| Camphor | 4.08 |
| Linalool | 1.09 |
| CIS-sabinene hydrate | 0.16 |
| Bornyl acetate | 0.01 |
| Alpha caryophylene | 0.20 |
| Terpinene-4-OL | 1.30 |
| L-dihydrocarvone | 0.01 |
| Myrtenal | 0.09 |
| Acetophenone | 0.05 |
| Alpha-humulene | 1.25 |
| Alpha-terpineol | 1.66 |
| Borneol | 1.03 |
| Verbenone | 0.06 |
| Neryl acetate | 0.08 |
| Carvon | 0.24 |
| Genranyl acetate | 0.03 |
| 4-methylacetophenone | 0.02 |
| Cuminic aldehyde | 0.04 |
| Myrtenol | 0.11 |
| 2-phenylethyl acetate | 0.03 |
| L-carveol (trans) | 0.20 |
| P-cymene-8-OL | 0.48 |
| Benzyl acetaone | 0.90 |
| 2-phenylethyl alcohol | 0.04 |
| B.H.T. | 0.01 |
| Methyl cinnamate | 0.16 |
| Thymol | 0.01 |
| P-methoxy acetophenone | 0.04 |
| Carvacrol | 0.72 |
| Others | 18.63 |

As shown in the above-described table, many components having aromatic and insecticide functions are contained in the sell flower essential oil. However, it is not clear what component participates in what way. It appears that a combination of a plurality of components displays excellent insecticide, bactericide, antivermin and antibacterial effects.

The insecticides and bactericides of the present invention are characterized in that sell flower essential oil comprising the aforementioned components extracted from sell flower is diluted with a solvent and adsorbed, mixed or dispersed into a carrier.

The sell flower essential oil has a sufficient insecticide effect even if it is diluted to 1%. Therefore, if the sell flower essential oil is adsorbed into a carrier, it is preferably diluted by a solvent to 2%, more preferably, 1% or less.

As the carrier, a mixture of one or two kinds or more of synthetic resin, diatomaceous earth, alumina, acid clay, wood powder, kaolin, bentonite, active carbon, silica, etc. can be employed, and sell flower essential oil is immersed therein and kneaded to thereby obtain granular insecticides and bactericides.

As the carrier, a suitable sheet material such as paper, cloth or the like can also be used. Diluted oil is directly immersed into the sheet material or adsorbed into adsorption particles, and the resultant material is introduced into the sheet material by mixing it into paper whereby sheet-like sell flower essential oil insecticides and bactericides are obtained.

Furthermore, an emulsifier, a dispersion agent, a suspension agent, a wetting agent, a stabilizer or the like is added according to the intended use in the form of an oil agent, an emulsion, a hydrate, a powdery agent, a tablet, a gelling agent, a jetting agent or the like.

The insecticides and bactericides made of sell flower essential oil according to the present invention can be used in a suitable combination with other insecticides, antivermin agents, perfumes, bactericides, fungicides, antioxidizers or the like.

The insecticides and bactericides made of sell flower essential oil according to the present invention have excellent vermicide, antivermin and antibacterial effects and are not harmful to humans or animals and have aroma. Therefore, they are advantageously used as an aromatic agent.

BRIEF DESCRIPTION OF THE DRAWING

The drawing is a graphic representation showing the results of termite tests with various concentrations of sell flower essential oil according to embodiments of the present invention.

DESCRIPTION OF THE PREFERRED EMBODIMENTS

Embodiment 1

Sell flower essential oil was obtained from leaves of sell flower by a steam distillation method. The obtained oil is dissolved with ether and then immersed into paper so as to be present in an amount of 1.0%, 0.5% and 0.1% by weight and dried for four hours. Thereafter, distilled water in an amount of 3.5 cc is added thereto and 30 working termites and 3 soldier termites are charged and left in an isothermic unit for 14 days. The number of deaths and the status of death were observed. The results are shown in the drawing. It can be seen from the drawing that termites were annihilated in one day with 1.0% concentration, in 5 days with 0.5% concentration and in 13 days with 0.1% concentration.

The antivermin effect is represented by the effect with respect to termites. Similar tests were conducted for cockroaches and dog ticks. As a result, it has been assured that there were also excellent insecticide results therefor. Similarly, effectiveness tests were conducted for three kinds of molds including *Cladosporium cladosporioides, Fusarium proriferatum* and *Alternaria alternata*. As a result, it has been found that the obtained agent was effective for *Cladosporium cladosporioides* and *Fusarium proriferatum* but not *Alternaria alternata*.

Embodiment 2

A circular filter paper having a diameter of 5.8 mm is saturated with 0.28 ml of stock solution, 0.33 ml of 10% dilute solution and 0.33 ml of 5% dilute solution. The filter paper was laid on the bottom of a petri dish. About 50 long-hair powder cockroaches were put on the filter paper and Japanese paper was covered over the petri dish. Then, it was left for 24 hours at room temperature and at a humidity of 75% to check the death rate. As a result, the death rate of the long-hair powder cockroaches after 24 hours was 100% in all cases of stock solution, 10% dilute solution and 5% dilute solution.

Embodiment 3

The sell flower essential oil was adsorbed in adsorption particles having a particle diameter of 50μ or less such as active carbon, zeolite, etc. The residue of sell flower after steam distillation and fibers of stems of sell flower were used to make paper, and the sell flower essential oil adsorbed in said adsorption material was mixed in the rate of 1 g per sheet of paper of dimension of 180 cm×90 cm to obtain a sheet of insect control paper of sell flower. Since the adsorption particles adsorbed with the sell flower essential oil are mixed when making paper, the sell flower essential oil is uniformly distributed within the paper. The insecticide effect was longer than the case of immersion after making paper. And, the antivermin paper has a high ornamental value as well as unique hand and feel of sell flower. If it is employed for wall paper, sliding doors, screens, etc., fixtures having the insect control effect are obtained.

Embodiment 4

Sell flower essential oil was obtained from leaves of sell flower by a steam distillation method. The essential oil was heated and mixed with granular butyl vinyl acetate so that the sell flower essential oil is immersed into the butyl vinyl acetate to obtain sell flower essential oil insecticides and bactericides in the form of pellets.

An antibacterial test of the sell flower essential oil insecticides and bactericides with respect to linea alba bacterium was conducted in the following manner.

Trichophyton mentagrophytes as test bacterial stock was inoculated with 5% blood Saburo agar-agar (Eiken Kagaku K.K.), and cultured for 10 days at 25° C., after which spores of about $10^6$/ml were floated on a 0.005% sulfosuccinnic acid dioctyl sodium solution to obtain a bacterial liquid. The bacterial liquid was added in the rate of 1 ml to 150 ml of measuring media formed from Saburo agar-agar media (made by Eiken Kagaku) and mixed, and the resultant mixture was poured into a petri dish 15 ml by 15 ml and solidified to provide a flat plate media for testing. One, three and five of the pellet-like sell flower essential oil agents were placed on the central portion of the flat plate media for testing and sealed and cultured for 14 days at 25° C. The presence or absence of the growth impeding zone around the agent was determined by naked eye observation. As a result, in the case of one pellet, the impeding zone was slightly recognized. And it was confirmed that the antibacterial effect with respect to white linea alba bacterium was excellent.

Embodiment 5

Sell flower essential oil extracted from sell flower was dispersed by triglyceride to improve affinity with solvent (water) and obtain a liquid sell flower essential oil antivermin agent. Since the thus obtained sell flower essential oil antivermin agent is liquid, it can be filled into a spray vessel so that the agent is sprayed for use.

What is claimed is:

1. An insecticidal and bactericidal composition comprising essential oil distilled from sell flow (Alpinia Speciosa K. schum) in combination with a carrier for said essential oil selected from the group consisting of granules, paper, sheets, pellets and a liquid containing a dispersant for the essential oil.

2. A composition according to claim 1, prepared by contacting a solvent solution of the essential oil with the carrier.

3. A composition according to claim 2, wherein the carrier is in the form of a sheet.

4. A composition according to claim 3, wherein the carrier is paper.

5. A composition according to claim 2, wherein the carrier is in the form of granules.

6. A composition according to claim 5, wherein the granules are of diatomaceous earth, alumina, acid clay, wood powder, kaolin, bentonite, actived carbon or silica.

7. A composition according to claim 1, wherein the carrier is in the form of pellets.

8. A composition according to claim 1, wherein the carrier is a liquid containing a dispersant for the essential oil.

9. A composition according to claim 8, wherein the liquid is water.

* * * * *